United States Patent [19]

Hidaka et al.

[11] Patent Number: 5,225,199

[45] Date of Patent: Jul. 6, 1993

[54] PHARMACEUTICAL PLASTERS

[75] Inventors: Osafumi Hidaka, Akigawa; Satoshi Murakami, Tachikawa, both of Japan

[73] Assignee: Teijin Limited, Osaka, Japan

[21] Appl. No.: 778,819

[22] PCT Filed: Apr. 23, 1991

[86] PCT No.: PCT/JP91/00541

§ 371 Date: Dec. 24, 1991

§ 102(e) Date: Dec. 24, 1991

[87] PCT Pub. No.: WO91/16044

PCT Pub. Date: Oct. 31, 1991

[30] Foreign Application Priority Data

| Apr. 24, 1990 | [JP] | Japan | 2-106422 |
| Jul. 17, 1990 | [JP] | Japan | 2-187094 |
| Aug. 1, 1990 | [JP] | Japan | 2-202408 |
| Aug. 1, 1990 | [JP] | Japan | 2-202409 |

[51] Int. Cl.$^5$ .................................. A61F 13/00
[52] U.S. Cl. ........................ 424/443; 424/448; 424/449; 602/57; 602/58; 604/304; 604/307
[58] Field of Search .......... 424/443, 448, 449; 604/304, 307; 602/57, 58

[56] References Cited

U.S. PATENT DOCUMENTS

| 3,598,123 | 8/1971 | Zaffaroni | 128/268 |
| 4,554,317 | 11/1985 | Behar | 604/304 |
| 4,743,499 | 5/1988 | Volke | 428/317.3 |
| 4,801,458 | 1/1989 | Hidaka et al. | 424/443 |
| 4,906,240 | 3/1990 | Reed | 604/307 |
| 4,915,102 | 4/1990 | Kwiatek | 604/307 |
| 4,990,340 | 2/1991 | Hidaka et al. | 424/449 |
| 4,997,425 | 3/1991 | Shioya | 604/304 |
| 5,035,893 | 7/1991 | Shioya | 424/445 |
| 5,045,319 | 9/1991 | Chien | 424/448 |
| 5,064,422 | 11/1991 | Wilk | 604/307 |

FOREIGN PATENT DOCUMENTS

| 0227836 | 7/1987 | European Pat. Off. |
| 8901345 | 2/1989 | European Pat. Off. |
| 0318385 | 5/1989 | European Pat. Off. |
| 0413034 | 2/1991 | European Pat. Off. |
| 57-181010 | 11/1982 | Japan |
| 60-75062 | 4/1985 | Japan |
| 63-297320 | 12/1988 | Japan |
| 64-40420 | 2/1989 | Japan |
| 1-308224 | 12/1989 | Japan |

Primary Examiner—Thurman K. Page
Assistant Examiner—D. Gabrielle Phelan
Attorney, Agent, or Firm—Sughrue, Mion, Zinn, Macpeak & Seas

[57] ABSTRACT

A plaster comprising the film layer which is composed of a film having 0.5 to 4.9 μm thickness, 8 to 85 g/mm strengths, respectively in the two directions intersecting substantially at right angle, 30 to 150% elongations, respectively in the two directions intersecting at right angle, and 1.0 to 5.0 ratio between the two direction elongations (wherein the smaller elongation is used as the denominator, when the ratios of the elongations in the 2 directions are different) and an adhesive layer (a) which contains a transdermally absorbable drug and is laminated on one surface of said film layer in 2 to 60 μm thickness enables transdermal absorption of a clinically effective amount of a drug with skin rashes reduced. Additionally, a backing sheet may be preferably provided, for example, the plaster made of said film layer (3) and said adhesive layer (a) (4) is press-bonded via an adhesive layer (b) (2) to a backing sheet (1) and a release film (5) to give a plaster of improved handleability.

33 Claims, 1 Drawing Sheet

PHARMACEUTICAL PLASTERS

FIELD OF THE ART

The present invention relates to pharmaceutical plasters which can be used in treatment for a variety of diseases.

BACKGROUND OF THE ART

As the administration routes of medicines, ointments or the like have been frequently used as a local administration in addition to conventional ones such as oral, injection or rectal administrations. Further in recent years, the technical development has made steady progress in transdermal application of systemically acting drugs and several kinds of drugs have come to be clinically used in practice.

Since the transdermal administration of drugs enables them to avoid the first-pass effect which they would suffer in liver, if they were orally given, drug concentration in blood is far more stable than in the case of oral or injection administration, and many advantages also can be obtained, for example, longer effective time, easier removal of the drug by detaching the preparation in case of serious side-effects, and the like.

These merits have received strong attention and changes of conventional oral route preparations to transdermal ones have been investigated on a variety of drugs.

As clinical application of the transdermal preparations has made advance, however, the difficulties and problems in the transdermal route have become clear.

Several of them are as follows:

(1) One of the most serious problems of the transdermal preparations is outbreak of local irritation and skin rash or contact dermatitis. According to a statistics, the incidence of rash is 20 to 50% by transdermal preparations of a typical occlusive type tape.

In many cases, however, the patients must use such preparations for their merits, even when the application of such preparations results in rash development.

Further, many of the drugs used clinically today are generally resistant to transdermal absorption and, even in the drugs which are transdermally absorbable, the absorption of the clinically effective amount needs enlarged application areas and combination of additives such as an absorption-promoting agent.

The enlarged application areas and the use of absorption-promoting agent and the like frequently bring about increased areas and aggravation of skin rash.

Thus, a transdermally applicable preparation which enables the absorption of a clinically effective dose of the drug with skin rash eruption inhibited is desired.

(2) In addition, while a transdermal preparation is applied for a long time, the preparation is stained or becomes peelable with time, especially bathing accelerates the removability.

It is troublesome, however, to apply a new plaster, every time the old one peels off. Moreover, the dose control becomes difficult, satisfactory efficacy cannot be attained and problems remain in appearance and hygiene.

Thus, a transdermal preparation which is resistant to staining and peeling are desired even after prolonged application.

(3) By the way, a transdermal preparation is of a sustained release type and particularly effective for chronic diseases or diseases requiring long-term treatment. And the patients with such diseases are elder people of high age in many cases. Generally, however, elder people are not good at handling which requires complicated operation.

Thus, a transdermal preparation is desired to be easy to handle for the patients, in addition to pharmaceutic satisfactions such as high absorption and the like.

Conventionally, as a plaster aiming at absorption of a clinically effective amount of a drug with skin rash inhibited, for example, the plasters according to the present inventors are known, which bear a knitted fabric of microporous hollow fibers as a constituent (WO 87/00046, WO 87/04343 and WO 90/09784).

Such plasters have been satisfactory for skin rash reduction and absorption of a clinically effective amount of a drug, but other more excellent plasters which cause no skin rash and resist peeling, even when applied for a more prolonged time, thus revealing sufficient efficacy with no problem of appearance, have been still desired.

In other words, an object of the present invention is to provide a pharmaceutical plaster which can enable the absorption of a clinically effective amount of a drug causing extremely reduced skin rash and no breakage and no peeling from the skin because of its satisfactory stretchability enough to follow skin contraction and expansion.

Another object of the present invention is to provide a pharmaceutical plaster which has excellent handleability in addition to the good absorption of a clinically effective amount of a drug, extremely reduced skin rash, no breakage and no peeling because of good stretchability to follow skin contraction and expansion.

Further, another object of the present invention is to provide a pharmaceutical plaster which can expect to develop sufficient clinical efficacy with a reduced content of a drug, when an expensive bulk such as buprenorphine or buprenorphine hydrochloride or a drug which is desired to reduce the remaining after application according to the legislation on psychopharmaceuticals handling is employed.

DISCLOSURE OF THE INVENTION

The present inventors have made intensified studies on the measures for the plasters which can utilize the advantages of conventional transdermal preparations with skin rash decreased, enable the absorption of a clinically effective amount of drugs of as many kinds as possible even if they are resistant to transdermal absorption and have excellent handleability, and attained the present invention.

In other words, the present invention is a plaster comprising (1) a film layer which is composed of a film having a thickness of 0.5 to 4.8 $\mu$m, a strength of 8 to 85 g/mm, elongations of 30 to 150% in the two directions intersecting substantially at right angle, respectively, and the elongation ratio of 1.0 to 5.0 (wherein the smaller elongation is used as the denominator, when the ratios of the elongations in the two directions are different). and (2) an adhesive layer (a) which is laminated all over the above-stated film layer in 2 to 60 $\mu$m thickness and contains transdermally absorbable drugs.

Moreover, the present invention is a plaster comprising (1) a film layer which is composed of a film having a thickness of 0.5 to 4.9 $\mu$m, a strength of 8 to 85 g/mm and elongations of 30 to 150% in the two directions intersecting substantially at right angle, respectively, and the elongation ratio of 1.0 to 5.0 (wherein the smaller elongation is used as the denominator, when the ratios of the elongations in the two directions are different), (2) an adhesive layer (a) which is laminated on one surface of said film layer in 2 to 60μ thickness and contains transdermally absorbable drugs, and (3) a backing sheet which is laminated through an adhesive layer (b), with a higher adhesive force than 3 g/12 mm, partially or wholly on the other-side surface of said film layer whose one-side surface has said adhesive layer (a) laminated.

Moreover, the present invention is a plaster comprising (1) a film layer (a) which is composed of a film having a thickness of 0.5 to 4.9 μm, a strength of 8 to 85 g/mm and elongations of 30 to 150% in the two directions intersecting substantially at right angle, respectively, and the elongation ratio of 1.0 to 5.0 (wherein the smaller elongation is used as the denominator, when the ratios of the elongations in the two directions are different), (2) an adhesive layer (a) which is laminated on one surface of the above-stated film layer in 2 to 60μ thickness and contains transdermally absorbable drugs, (3) a backing sheet which is laminated through an adhesive layer (b1), with a higher adhesive force than 3 g/12 mm (a1), partially or wholly on the other-side surface of said film layer (a) whose one-side surface has said adhesive layer (a) laminated, and (4) a film layer (b) a film having 0.5 to 4.9 μm thickness, 8 to 85 g/mm strength, 30 to 150% elongations in the two directions intersecting substantially at right angle and 1.0 to 5.0 elongation rate (wherein the smaller elongation is used as the denominator, when the ratios of the elongations in the two directions are different), and is laminated through an adhesive layer (b2) with an adhesive force higher than 3 g/12 mm (b1), partially or wholly on the other-side surface of said backing sheet whose one-side surface is adhered to the adhesive layer (b1).

BEST EMBODIMENT OF THE PRESENT INVENTION

Figure 1:
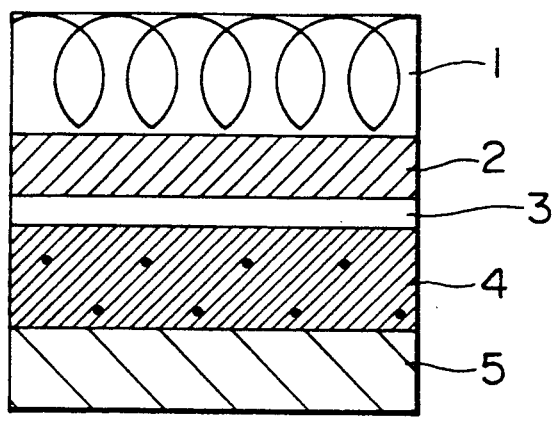
FIG. 1 depicts the cross section of the plaster which has been prepared in Example 1 of the present invention. In the figure, 1 means the backing sheet (hollow fiber sample); 2, the adhesive layer (b); 3, the film layer (polyethylene terephthalate film); 4, the adhesive layer (a) (the progesterone-containing layer); and 5, a release liner (it can be peeled off, when the plaster is applied).
Figure 2:
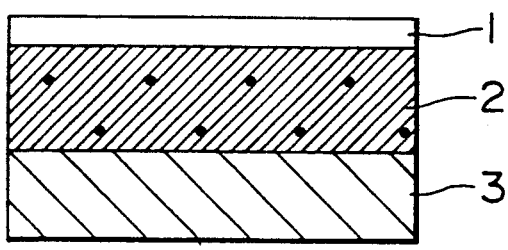
FIG. 2 depicts the cross section of the plaster which has been prepared in Example 4 of the present invention. In the figure, 1 is the film layer (polyethylene terephthalate film); 2, the adhesive layer (a) (progesterone-containing layer); and 3, a release liner.
Figure 3:
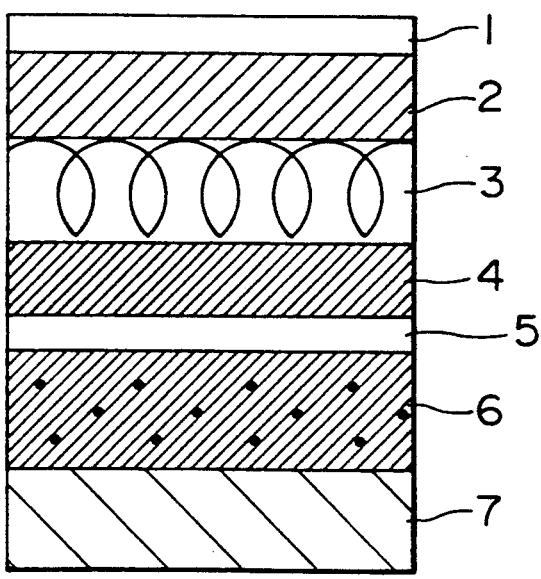
FIG. 3 depicts the cross section of the plaster which has been produced in Example 22 of the invention. In the figure, 1 means the film layer (b) (polyethylene terephthalate film); 2, the adhesive layer (b2); 3, the backing sheet (hollow fiber sample); 4, the adhesive layer (b1); 5, the film layer (a); 6, the adhesive layer (a) (estradiol-containing layer) and 7, the release liner.

The plasters according to the present invention have a film layer which is composed of a film of 0.5 to 4.9 μm thickness, 8 to 85 g/mm strengths and 30 to 150% elongations in the two directions intersecting substantially at right angles, respectively, and 1.0 to 5.0 elongation ratio (wherein smaller elongation is used as the denominator, when the elongation ratio is different in the two directions). In order to reduce skin rash, it is important, first of all, to reduce the physical stimulation caused by the plaster preparations. Thus, the film thickness is decreased to less than 4.9μ, preferably less than 4.0μ, because skin stimulation is weakened, as the film becomes thin. Particularly, less than 3.5 μm is preferred, since this tendency becomes pronounced. In the meantime, plasters are used by applying them to human skins and required to follow the expansion and contraction of the skins in body actions to some extent. The films may be often broken, when they are extremely thin, while the skin stimulation becomes severe, when they hardly follow the skin stretching. It was found that the physical stimulation scarcely changed, even when the thickness was reduced to less than 0.5 μm, in addition, the production of the plaster became troublesome.

The purposes of using the film layer as a substrate are to increase the seal tightness at the plaster application sites and promote the transdermal absorption, to cover the adhesion surface with the film and prevent the adhesive from sticking to clothes or other skin areas, and the like. As the film becomes thin, the seal tightness lowers, less than 5 μm reveals a tendency to decrease the tightness and less than 1 μm, particularly less than 0.5μ becomes difficult to ensure the satisfactory seal tightness as a plaster.

As for the film strength, higher than 85 g/mm, respectively, in the two directions intersecting substantially at right angle cannot reduce the physical stimulation sufficiently, however the film thickness is thin, while less than 8 g/mm is apt to cause breakage of the plasters on or during the application and they cannot be used with high reliability.

As for the film elongation, over 150%, respectively, in the two directions intersecting substantially at right angle give the handleability damage, while less than 30% increases the physical stimulation and raises the frequency in film breakage on application.

Further, according to the investigation results by the present inventors, a film having the elongation ratio of 1.0 to 5.0 in said two directions (wherein the smaller elongation is used as the denominator, when the elongations are different in the two directions), preferably of 1.0 to 3.0, is preferably used to improve the application feeling. The films of over 5.0 ratio, namely of extremely low elongation in one direction, cannot follow the expansion and contraction of the skin satisfactorily to cause several problems or troubles, for example, making the application feeling unpleasant because of skin stretched, making the film easier peelable and damageable, thus being concluded to be unsuitable.

Accordingly, the film of the invention has 0.5 to 4.9 μm thickness, 8 to 85 g/mm strengths, respectively, in the two directions intersecting substantially at right angle, 30 to 150% elongations, respectively, in the two substantially rectangular directions, and 1.0 to 5.0 elongation ratio in said two directions (wherein the smaller elongation is used as the denominator, when the ratios of the elongations in the two directions are different). Particularly, the film is preferred, which has less than 3.5 μm, more preferably 0.5 to 2.0 μm thickness, 8 to 85 g/mm strength, 45 to 150% elongations and 1.0 to 3.0 elongation ratio.

The strength in the present invention shows a value which is obtained by measuring the maximum load at break of a film according to the measurement of tensile strength of plasters in Japanese Pharmacopoeia and turning the result into the load per unit length (g/mm) and the elongation means the elongation at break (%). The two directions intersecting substantially at right angle means so-called lengthwise direction and widthwise direction.

In the present invention, said film is preferably desired to have good stability with the passage of time and high safety such as resisting allergic reactions, when applied. Such films include polyolefins, for example, polyethylene or polypropylene; polyesters, for example, polyethylene terephthalate or polyethylene naphthalate; polyamides, for example, nylon 6 or nylon 66; ethylene-vinyl acetate copolymer and the like. They can be used alone or may be used in a composite or laminated form.

Among these films, polyester films are preferred. Polyester films have generally high stability to heat and light, low drug absorption, poor interaction with drugs and high safety to humans. In addition, the film of the thickness specified above is preferred, because it has a proper level of seal tightness to moderate the moisture permeability, thus holding the moisture content in the corneal layer at a level enough to help the transdermal absorption of the drug at the plaster application site.

Polyethylene terephthalate films are preferred among polyester films.

Especially, when an ultrathin film of less than 3.5 μm thickness, 8 to 85 g/mm strength and 45 to 150% elongation is used, stabilized plastering is possible for a prolonged time, even when the adhesive layer (a) is less than 30 μm thick.

Further, it is surprising that, when a more ultra thin film of 0.5 to 2.0 μm thickness, 8 to 85 g/mm strength and 45 to 150% elongation is used, the plaster can be applied to human skin with satisfactory stability, even when the adhesive layer (a) is 2 to 15μ thick, particularly less than 10 μm.

It is possible to prepare a plaster having a, for example, 10 μm thick adhesive layer on a 5 to 20 μm thick film (of usual thickness). But, this case is quite different, to be surprised, from the plaster of the present invention, having a 10 μm thick adhesive layer on a 0.5 to 4.9 μm particularly 0.5 to 2.0 μm thick film, in the adhesion to human skin and its stability, and an ultra thin film is markedly superior. One of the reasons is probably because human skins have microscopic unevenness, and the films of usual thickness cannot follow the unevenness, while the film according to the invention can do and sufficient adhesion is attained even with a extremely small amount of the adhesive layer.

In other words, the present invention can produce a plaster which has high stability, a reduced dose of a drug and minimized skin rash, differing from the conventional plasters by laminating a thin adhesive layer containing the drug on an ultra thin film of specified strength and elongation.

In the present invention, a polyester film is preferably used as the above-stated film layer. Usually, polyester films include a small portion of solid fine particles for improving the slipperiness. But, there was no sufficient information to know what kinds of influence such solid particles will exert on plasters, for example, of the present invention.

The present inventors have energetically investigated these subjects and found that 0.01 to 1 wt. % solid fine particle content in the polyester film, 0.01 to 3.0 μm average particle size and the average particle size of less than 1.5 time film thickness are especially important to reduce skin rash, as the absorption of a clinically effective amount of a drug is maintained.

Such solid fine particles include inorganic or organic fine particles of, for example, (1) silicon dioxide, (2) alumina, (3) silicate salts or aluminosilicate compounds containing more than 30 wt. % of silicon dioxide components, (4) one or more oxides of metals selected from magnesium, zinc, zirconium ant titanium, (5) one or more sulfates of metals selected from calcium and barium, (6) one or more phosphates of metals selected from lithium, sodium and calcium, (7) one or more terephthalate salts of metals selected from calcium, barium, zinc and manganese, (8) one or more titanate salts of metals selected from magnesium, calcium, barium, iron, cobalt, manganese and nickel, (9) one of metals selected from calcium and magnesium, (11) carbon, (12) glass and (13) cross-linked polystyrene. As a matter of course, they may be in a single form or in a mixed form of 2 or more different kinds of the particle.

Less than 0.01 wt. % solid fine particle content is not desired because the prevention of skin rash oftentimes becomes insufficient, and over 1 wt. % is also undesirable as a pharmaceutical preparation because the transdermal absorption of the drug sometimes becomes difficult to reach a sufficiently satisfactory level. Further, less than 0.01 μm average particle size sometimes causes insufficient film slipperiness, resulting in unsatisfactory film handleability and do sometimes insufficient prevention of skin rash. Average particle size more than 3.0 μm or more than 1.5 time film thickness causes unsatisfactory transdermal drug absorption in some cases. In such cases, it is presumed that moisture transpiration and permeability become too large due to the voids around the solid fine particles in the film layer.

This film layer plays a role of a substrate (backing) layer for the adhesive layer, as preventing the skin from erupting rash, when the plaster is composed of the film layer and the adhesive layer (a). Further, in the case where the plaster of the invention comprises this film layer, the adhesive layers (a) and (b) and a plane substrate, this film can be used as the backing sheet, too, and, in this case, the film layer used as the backing sheet has the role to improve the handleability. When the plaster of the invention comprises the film layer (a) and the film layer (b), the former film plays a role of backing the adhesive layer (a), as preventing the skin from erupting rash, while the latter improves the handleability.

The plaster according to the present invention has the adhesive layer (a) which is composed of an adhesive containing transdermally absorbable drugs and is spread on one surface of the above-stated film layer in 2 to 60 μm thickness.

Generally, the adhesive layer plays a role of retaining a needed amount of the principal ingredient, namely transdermally absorbable drugs, and stabilizing the application of the plaster to the skin, but a various kinds of solvents remaining in the adhesive layer after the layer formation become one of the major causes of rash eruption. Accordingly, if the adhesive layer can play these roles satisfactorily, its layer thickness is preferably as thin as possible because of easy removal of the remaining solvents and economic reasons.

In the present invention, because the above-stated specific films are used as the film layer, the thickness of the adhesive layer more than 2 μm can extremely reduce the peeling of the plaster during the application, and less than 60 μm, preferably less than 30 μm, can reduce skin rash caused by the remaining solvents because the remaining solvents themselves can be reduced to less than 100 ppm, more preferably less than 50 ppm as required, and stabilize the application with a needed amount of the drug retained.

As the adhesive including the drugs used in the present invention, a usual adhesive is used and can be selected from, for example, a rubber viscous composition such as silicone rubber, polyisoprene rubber, styrene-butadiene copolymer rubber, acryl rubber or natural rubber; a vinyl viscous composition such as a polyvinyl alcohol (PVA) or an ethylene-vinyl acetate copolymer; a viscous composition mainly containing, for example, a silicone adhesive, a polyurethane elastomer, polyester elastomer or polybutadiene elastomer; acrylic resin and the like. Particularly an acrylic resin is preferably used and, from the view points of more reduced skin irritation, proper tackiness and adhesion, high cohesion and high solvent resistance, an acrylic resin which is prepared by copolymerization of (1) at least 80 to 98 mole % of an alkyl (meth)acrylate in which the alkyl is of 4 or more carbon atoms and (2) 2 to 20 mole % of acrylic acid and/or methacrylic acid. The examples of alkyl (meth)acrylate whose alkyl group is of 4 or more carbon atoms are butyl (meth)acrylate, amyl (meth)acrylate, hexyl (meth)acrylate, heptyl (meth)acrylate, octyl (meth)acrylate, nonyl (meth)acrylate, decyl (meth)acrylate, 2-ethylhexyl (meth)acrylate and the like. These adhesives may be used alone or in 2 or more combination.

As stated above, the plaster comprising the film layer specified in the present invention and the adhesive layer of a specified thickness containing transdermally absorbable drugs is an extremely thin laminated product and desires careful handling in some cases so that film damage, blocking between the adhesive layers (a) and (b) or the like may not occur.

In the plaster of the present invention, a backing sheet can be laminated via the adhesive layer (b) onto said film layer by adhering the sheet partially or entirely to the one face of the film layer opposite to the other surface on which the adhesive layer (a) is laminated, with an adhesion force of higher than 3 g/12 mm.

Such backing sheet may be left on the plaster as it is, but can be also used for leaving the film layer and the adhesive layer (a) on human skin by applying the plaster, then removing the sheet therefrom.

The lamination of such a backing sheet decreases the curling of the plaster and the damages and facilitates the application by patients themselves.

The backing sheet which can be used in the present invention is films, nonwoven fabrics, paper-like substance and/or cloth such as woven or knitted fabrics or their combination. In the case where the backing sheet of the present invention is removed after application of the plaster, there is no specific limitation to these materials, but in the case where the material remains laminated after application, the sheet is preferably flexible and suitably stretchable without disturbance of moisture permeation of the film layer so that the plaster can prevent skin rash and follow the expansion and contraction of the skin.

When the backing sheet of the present invention is film, the base material for such film are, for example, polyolefins such as polyethylene or polypropylene; polyesters such as polyethylene terephthalate or polyethylene naphthalate; polyamides such as nylon 6 or nylon 66; ethylene-vinyl acetate copolymer, polyvinyl alcohol and the like. Among the backing sheet materials made of these films, microporous films are preferred because the moisture permeability of the film layer of the invention is not disturbed.

Particularly, the films having the thickness, strength and elongation which are specified in the present invention are preferred, further the polyester films containing the above-defined amount of solid fine particles of the above-defined particle sizes are more particularly preferred.

When the backing sheet is cloth such as nonwoven fabric, paper-like substance or woven or knitted fabric, yarns made of synthetic fiber base materials such as nylon, polyester, acrylic or urethane fibers or natural or regenerated fibers such as cotton, rayon, acetate or the like can be used in the single form or in combination.

Among these nonwoven fabrics, paper-like substances, woven or knitted fabrics, knitted fabrics are preferred as a backing sheet, because they little irritate skins.

Particularly, the knitted fabrics of 10 to 300 g/m$^2$ can be cited. Such fabrics scarcely cause skin irritation and exert very little influence on the moisture permeability of the film layer. Further, the fabrics hardly lose their flexibility, even when the knitted fabric is laminated to the film layer. This is presumably because the allowance in the delicate fiber structure of the knit can absorb the external stress. Moreover, it is very surprising that both the tackiness of the plaster to the human skin and the adhesion of the knitted fabric to the film layer are stabilized despite that a backing sheet made of a markedly heavy and voluminous knitted fabric is bonded via a very thin adhesive layer to the human skin with a relatively small tackiness. Thus, the use of the adhesive layer (a) and the film layer can be decided independently from the backing sheet. When the unit area weight of the fabric is less than 10 g/m$^2$, the handleability is little improved, while more than 300 g/m$^2$ leads to so high bulkiness that bad appearance comes about undesirably. Additionally, too high bulkiness frequently causes the plaster to be involuntarily peeled off because the hand often hits the plaster, when it wanders near.

Such knitted fabrics give desirable results, particularly when they made from hollow fibers having through holes radially extending toward the outer periphery.

The hollow fibers having through-holes radially extending toward the outer periphery are preferably the hollow fibers having fine pores which distribute all over the cross section and are arranged in the fiber-axis direction, and at least a part of which connect through to the hollow part.

The cross section shapes of the outline and the hollow of the hollow fiber according to the invention may be any. There may be the cases, for example, where both of the outline and the hollow section are round, or one of them is round, while the other is modified, or both are modified similarly or dissimilarly. Further, there is in no need of special limitation to the outer size of fibers.

The outer size (filament thickness) of such hollow fibers is preferably 4 to 45μ diameter. More than 45μ size causes too high skin irritation. Less than 4μ is accompanied by poor handleability.

The percentage of hollowness of the fibers in the present invention may be optional but more than 5% is preferred, and the area proportion of the through-holes extending toward the outer periphery to the fiber cross section is preferably 0.01 to 70%, particularly preferably 0.01 to 50%, more preferably 1 to 50% based on the cross section area after the hollow part is subtracted.

Such knitted fabrics are satisfied, if they are mainly made of the above-stated hollow fibers and fibers other than hollow fibers may be partially mixed as long as the effect which the invention aims at is not affected.

The material which constitutes the hollow fibers is particularly preferably polyethylene terephthalate which does not interact with drugs with high stability and high safety.

The polyethylene terephthalate hollow fibers to be used in the present invention can be produced by the methods described in, for example, Japanese Patent Laid-open No. 56-20612 (1981), Japanese Patent Laid-open No. 56-20613 (1981), Japanese Patent Laid-open No. 43420 (1981) and the like.

This backing sheet and the film layer are laminated with the adhesive layer (b). The adhesive which can be used as the adhesive layer (b) are, in addition to a variety of usual pressure-sensitive adhesive exemplified as an adhesive for the adhesive layer (a), other adhesives such as polyvinyl acetate adhesive, for example, ethylene-vinyl acetate copolymer, polyvinyl pyrrolidone, sorbitol, starch and the like.

An acrylic resin is preferred as an adhesive for the adhesive layer (b), particularly an acrylic resin which is produced by copolymerization of (1) at least 80 to 98 mole % of an alkyl (meth)acrylate wherein the alkyl is of 4 or more carbon atoms and (2) 2 to 20 mole % of acrylic and/or methacrylic acid from the view points of reduced skin irritation, adequate tackiness or adhesion, high cohesion and excellent solvent resistance. The alkyl (meth)acrylates wherein the alkyl is of 4 or more carbon atoms is, for example, butyl (meth)acrylate, amyl (meth)acrylate, hexyl (meth)acrylate, heptyl (meth)acrylate, octyl (meth)acrylate, nonyl (meth)acrylate, decyl (meth)acrylate, 2-ethylhexyl (meth)acrylate and so on. These adhesives may be combined.

Or, in the cases where the backing sheet is removed after application of the plaster, as an adhesive for adhesive layer (b), PVA (polyvinyl alcohol), ethylene-vinyl acetate copolymer, polyvinyl pyrrolidone, sorbitol, starch or above-stated vinyl acetate adhesive can be cited.

When PVA or polyvinyl acetate is used as an adhesive for adhesive layer (b), PVA of 100 to 2,000 average polymerization degree and 3 to 20% concentration and polyvinyl acetate of 100 to 1,000 average polymerization degree and 3 to 20% concentration can be cited.

Particularly, good results will be readily obtained, when woven or knitted fabrics are used as the backing sheet and PVA or the like is used as the adhesive.

In other words, the backing sheet is adhered to the film layer during the plaster handling, then can be removed if needed, after application to human skin. But, the plaster is kept in an air-tightly sealed aluminum foil-laminated pouch before use and, if the solvents such as methanol, ethyl acetate or water remains in the adhesive layer after lamination of the sheet to the film layer, they tend to move and diffuse into the adhesive layer (a) containing the drugs during the storage. Thus, skin rash may develop and deterioration of the drug occurs with the passage of time in some cases.

In order to remove such troubles or inconveniences, the solvents used in lamination of the sheet and the film layer should be completely removed, but it is difficult, when the sheet is made of a film layer, and special ideas or techniques are needed in the production process. In this case, the plaster of the present invention employs a specific film as a backing and the reduction in production efficiency tends to occur due to film breakage, wrinkling and the like, if complicated processes are included in the production. On the contrary, the backing sheet of woven or knitted fabric can easily release the vapor of solvents through the meshes, thus preferred embodiments of complete solvent withdrawal can be realized.

Particularly, the backing sheet of woven or knitted fabric and a film are put together, an adhesive solution is applied from over the fabric, and they are heated, thus sufficient adhesion can be effected without any anxiety of solvent remaining. Or an adhesive is applied to the sheet of woven or knitted fabric and dried beforehand, then the material is laminated on the film layer directly as it is or after heating or air-drying to remove the remaining solvents, when needed. The adhesive layer containing the drug can be laminated either before or after the lamination of the sheet, but preliminary lamination between the film layer and the sheet is preferred as drugs are generally unstable to heat.

In the present invention, the backing sheet may be partially or entirely adhered to the surface of the film layer, but troubles such as peeling off of the extremely thin film tend to happen, when only the sheet is removed after plaster application to human skin, even when the adhesion between the sheet and the film layer is small. In order to prevent this, it is one of preferred embodiments to provide the only overlapping but not adhered parts so that the entire surface of the film layer does not always stick to the sheet. The patients can peel off the sheet much easily from the not adhered part. It is one of useful techniques to place a film, paper, cloth or the like of 5 to 100 μm thickness between both of the surfaces for providing the surface having parts where the sheet is not adhered to the film layer.

It has been found that the patient can peel off the sheet with extreme easiness, when the not-adhered part is near the edge of the plaster. Moreover, since the patient peels off only the sheet from the edge by pulling it, for example, in 90° or 180° direction, the peeling off of the plaster from human skin and the breakage of the film layer are also reduced. It is particularly preferred, when the plaster is prepared from an extremely thin and skin irritation-reduced, thus strength-lowered film and the thin adhesive layer according to the present invention.

The film layer and the backing sheet are laminated, for example, by dissolving an adhesive in a solvent, forming the adhesive layer (b) on the film layer in a 2 to 100μ thickness, then pressing the backing sheet thereto. Or the adhesive layer (b) of 2 to 100 μm thickness is prepared beforehand and the layer is pressed to on one surface of the sheet and/or on one surface of the film layer, then the sheet and the film layer are adhered via the adhesive layer (b) to each other by pressing. The film layer and the sheet can be adhered via the adhesive layer in a part of these surfaces or can be adhered entirely all over the surfaces. Above all, in the case where the sheet is not removed off after application of the plaster, it is preferred to adhere them to each other through a part of these surfaces in a range where the sheet can be stably stuck to for a long period of time, because there happens no reduction in moisture permeability of the film layer. As an embodiment such as partial adhesion, is cited, for example, scattering spots of the adhesive layer (b) measuring 0.5 100 mm$^2$ sizes and 2 to 100 $\mu$m thickness or stripes of the adhesive layer (b) measuring 1 to 20 mm width and 2 to 100 $\mu$m thickness. Such partial adhesion can additionally relieve the skin irritation by the sheet with plaster handleability improved.

The thickness of the adhesive layer (b) is 2 to 100 $\mu$m, preferably 5 to 20 $\mu$m.

In the present invention, the adhesion strength between the backing sheet and the film layer is higher than 3 g/12 mm, and such strength is preferred because even the patients of high age can easily apply the plaster to the affected part without curling or breakage of the plaster.

The adhesion strength in the present invention is defined as a load (in grams) for peeling off the sheet or the film from a 12 mm wide laminate comprising the film layer and the sheet at a rate of 30 cm/minute in the 90° direction. When the laminate is partially adhered with spots or stripes of adhesive, the load (in gram) for peeling off the adhered part is measured and the value is converted to the one corresponding to 12 mm width (g/mm).

The adhesion strength can be suitably varied depending on the cases where the sheet is removed after application of the plaster to the affected part or not, or on the correlation of the adhesion strength of the film layer via the adhesive layer (a) to the skin. For example, if the adhesion strength between the sheet and the film layer is over 20 g/12 mm, the breakage of the film layer may possibly happen, when the backing sheet is removed from the film layer. Theoretically, the adhesion strength exceeds 20 g/12 mm, when the film strength is 8 to 85 g/mm, and it is thought that the film will not break even, for example, at 24 g/12 mm (2 g/mm). In the actual plasters, however, over 20 g/12 mm adhesion strength sometimes causes film breakage or the peeling of the plaster from the human skin. Less than 3 g/12 mm may cause delamination between the sheet and the film layer during the production, storage or handling. Accordingly, in the case where the backing sheet is removed after application of the plaster to the affected part, the adhesion strength preferably ranges from 3 g/12 mm to 20 g/12 mm, while in the case not to be removed, it can exceed 20 g/12 mm.

When the backing sheet is removed after application of the plaster to the affected site, the film layer manifests its merits fully during the application to attain the objects such as reduction in skin rash or the like.

Other measures for the same objects are disclosed in, for example, Japanese Patent Laid-open No. H1-51260 (1989). But, it did not make detail investigation on the structure of plaster as done in the present invention.

In the present invention, more desired plasters can be produced by controlling the "KOSHI" (a Japanese technical term on cloth touch or handle showing physical properties including flexural rigidity, compression modulus and instantaneous bouncing properties). The KOSHI of the backing sheet can be represented by a stiffness (cm$^3$/100) determined, for example, according to JIS P-8143, Stiffness Test, and the stiffness is preferably more than 0.08, particularly preferably more than 0.27.

Further, in the plaster comprising the above-stated film layer and the adhesive layer (a) according to the invention, a backing sheet can be partially or entirely laminated through the adhesive layer (b1) to film layer (a) on the other side surface of that to which the adhesive layer (a) is adhered, with an adhesion force higher than 20 g/12 mm, and another film layer (b) can be laminated partially or entirely through the adhesive layer (b2) to the backing sheet on the other side surface of that to which said adhesive layer b1 is laminated, with an adhesion force (b1) higher than 3 g/12 mm wherein the film (b) has 0.5 to 4.9 $\mu$m thickness, 8 to 85 g/mm strength, 30 to 150% elongations, respectively, in the two directions intersecting substantially at right angle and 1.0 to 5.0 ratio of the elongations in the two directions (wherein the smaller elongation is used as the denominator, when the ratios of the elongations in the two directions are different).

As the backing sheet for the plaster, can be cited moisture-permeating ones selected from the films, nonwoven fabrics, paper-like substances and cloth of woven or knitted fabrics which have been exemplified previously. In the present invention, the term, moisture-permeating sheets, means the sheets having a moisture permeability higher than 10 mg/day.cm$^2$, when the permeation is evaluated according to the method shown in the example (vi) of the present invention.

Among them, knitted fabrics are preferred and knitted fabrics of polyethylene terephthalate hollow fibers having 10 to 300 g/cm$^2$ unit area weight and through-hole pores extending radially toward the outer periphery, exemplified in the preferred embodiment of the backing sheet.

In other words, a plaster is desired to have adequately high transdermal absorption of the drug in addition to high flexibility, reduced skin rash and satisfactory handleability, and a proper level of tight seal is important for this purpose. In this case, it is preferred that a backing sheet made of a knitted fabric is laminated between adhesive layers (b1) and (b2), then film layer (b) is arranged on the outermost surface of the adhesive layer (b2) rather than a plaster coated with film layer (a) is simply laminated on adhesive layer (a). At this time, the knitted fabric not only plays a role of an interlayer for laminating the film layer (b) to make up for the lack of tight-sealing effect of the film layer (a), but also contributes significantly to the improvement in handleability of the plaster, further concerns the moisture retention, too. In addition, the knitted fabric is 10 to 300 g/m$^2$ in its unit area weight, thus having flexibility in the structure itself, and can delicately follow the contraction and expansion of skins to which the plaster is applied to decrease skin rash because of reduced physical stimulation to the affected site.

As a film for the film layer (b), are preferably cited similar base materials to those for the film layer (a).

Such a backing sheet and the film layer (b) are laminated via the adhesive layers (b1) and (b2) to the film layer (a), respectively, in the same manner as the backing sheet is laminated by pressing a part of the surface or the entire surface of the backing sheet to the film layer, by pressing the film layer (a) to a part or all of the backing sheet, and by pressing the backing sheet to a part or all of the film layer (b). The lamination can be conducted, as the backing sheet is laminated to the film layer (a) by pressing, by preparing the adhesive layers (b1) and (b2) separately and pressing them in turns, when needed, with heat, or by preparing separately laminate 1 of a backing sheet and the adhesive layer (b1), laminate 2 of the film layer (b) and the adhesive layer (b2) and laminate 3 of the film layer (a) and the adhesive layer (a) and then laminating free surface of the adhesive layer (b2) of the laminate 2 on the free surface of the backing sheet of the laminate 1, and then laminating free surface of the adhesive layer (b) on free surface of film layer (a) of the laminate 3.

In the particularly preferable process, the free surface of the adhesive layer (b) of the laminate 2 is laminated on the backing sheet, thus obtaining the laminate 4, then in turn, the free surface of the backing sheet of this laminate 4 is laminated on the adhesive layer (b1) followed by lamination of film layer (a), thus obtaining the laminate 5 which comprises, from top to down, film layer (b), adhesion layer (b2), backing sheet, adhesion layer (b1), and film layer (a). Then, free surface of the film layer (a) of the laminate 5 is laminated on the adhesive layer (a), or adhesive layer (a) is formed on the free surface of the film layer (a). In other words, any of the constituents of the plaster according to the present invention, namely film layer (b), adhesive layer (b2), backing sheet, adhesive layer (b1), and film layer (a), are thin and flexible, thus each of them desires handling with special caution, but such sequential lamination can facilitate the production. Especially the lamination process of adhesive layer (a) containing a drug is one of the most important stage influencing the content and the cost of the plaster of the present invention, and the use of laminate 5 as stated above enables stabilized production of plasters of uniform quality.

As an adhesive for the adhesive layers (b1) and (b2) used here, can be cited the same base material as of the above-stated adhesive (b). Particularly, the above-stated acrylic resins and the like are preferred. The thickness of these adhesive layers (b1) and (b2) is 2 to 100 μm.

Less than 2 μm thickness of the adhesive layer weakens the adhesion to the backing sheet to cause peeling of the backing sheet during application in some cases. More than 100 μm thickness tends to squeeze out the adhesive from the side face during plaster cutting or application, thus causing sometimes process troubles and contamination.

The particularly preferable thickness of adhesive layer (b2) ranges from 5 to 20 μm, while adhesive layer (b1), from 10 to 50 μm. The thickness of adhesive layer (b1) relates to the adhesion force of the plaster and extremely thinness is unsuitable.

In the plasters according to present invention, when the backing sheet and the film layer (b) are additionally laminated, the adhesion force is higher than 20 g/12 mm between the backing sheet and the film layer (a) and the film layer (b) is laminated to the backing sheet with 3 g/12 mm and higher adhesion force.

The plasters according to the invention has preferably more than 10 mg/day·cm$^2$ transpiration rate. Less than 10 mg/day·cm$^2$ tends to increase stuffiness, thus causing skin rash in some cases. On the contrary, there is a tendency to lower the transdermal absorption of the drug, when the moisture transpiration rate increases more than 80 mg/day·cm$^2$, and the transpiration rate ranges preferably from 10 to 80 mg/day·m$^2$.

The plasters of the present invention are connected partially or entirely through the adhesive layer (b), the adhesive layers (b1) and (b2) or the adhesive layer (c). The thickness of these adhesive layers is preferably as thin as possible, unless any hindrance or trouble occurs in the adhesion force, since the total thickness of the plaster can be reduced and peeling due to touching or hitting can be prevented. In many cases, generally it is enough with less than 20 μm, preferably less than 10 μm thickness.

The thickness of the adhesive layer (b1) is preferably 10 to 50 μm because the adhesion force to human skin tends to weaken as the thickness lessens.

In the meantime, the adhesive layer (a) is also desirably as thin as possible unless any trouble happens in adhesion, but the correlation of the compatibility between the drug and the adhesive with the dose also should be taken into consideration.

Generally, it has been known that the adhesion force of the plaster increases as the thickness becomes larger until it reaches about 50 μm and adhesive layers of 30 to 100 μm thickness are usually employed because stabilized adhesion force is realized. In the present invention, the use of ultra thin film layer (a) has improved the adhesion to human skin, thus the range from 5 to 30 μm can be adopted as a preferable thickness of adhesive layer (a).

As for the size of the plaster, namely the application area, the solubility and transdermal absorption change depending on the kinds of drugs and the sort of adhesives and some cases require expanded application areas in order to secure adequate transdermal absorption. As a matter of course, however, there is area limitation in human bodies to which the plaster is applicable, and area increase means dose increase, thus the area should be minimized as needed. Usually, about 5 to 200 cm$^2$ is preferred for good handle-ability.

The drugs used in the present invention are, for example, isosorbide dinitrate, nitroglycerin, buprenorphine (BN) hydrochloride, morphine, estradiol, progesterone, ketotifen, vinpocetine, nicotine and their derivatives and other known transdermally absorbable drugs and they can be used in a single form or in combination in 0.1 to 20% concentration in the adhesive.

The present invention is very desirable because an extremely thinned adhesive layer can be provided to lower the dose of the drug largely, when the drug is expensive or overdose causes any skin damage or abnormal transdermal absorption. Such drugs are, for example, narcotic analgesics such as buprenorphine hydrochloride or morphine and hormone preparations such as estradiol or progesterone derivatives.

The plasters of the present invention may include solubilizers, diffusion auxiliaries, fillers and the like, when needed.

As a diffusion auxiliary used in the present invention, are cited, for example, alcohols such as glycerol, diethylene glycol, polyethylene glycol, higher fatty acid alcohols; dimethyl sulfoxide and its alkylmethyl derivatives; salicylic acid, urea, dimethylacetamide, dimethylformamide, lanolin, allantoin, squalene, carbopol, diisopropyl adipate, lauryl pyroglutamate, ethyl laurate, methyl nicotate, sorbitol and pyrrolidone derivatives such as dodecylpyrrolidone or methylpyrrolidone; olive oil, castor oil, fluid paraffin and camphor.

The filler is, for example, water, titanium oxide, calcium carbonate, gypsum, calcium silicate, aluminum silicate, kieselguhr, carbon black, Indian red, a variety of face cleaners, lactose, perfumes, deodorants and powders or formed products of synthetic resins such as polyethylene, polypropylene, polyester or polystyrene.

EXAMPLES

The present invention will be illustrated in more detail using examples and comparative examples. The parts in the examples mean parts by weight and the properties in the examples were measured by the following procedures:

(i) Water absorption rate (based on JIS-L 1018)

The fibers are knitted and the knitted fabric is washed prescribed times in a domestic washing machine with 0.3% aqueous solution of an anionic detergent (ZABU produced by KAO) at 40° C. for 30 minutes, then dried. The sample is extended horizontally and a drop of water (0.04 cc) is allowed to fall from the height of 1 cm and the time is measured until the water is completely absorbed and the reflection light cannot be noticed.

(ii) Water absorption percentage

The sample obtained by drying the knitted fabric is dipped in water longer than 30 minutes, then dehydrated for 5 minutes with the centrifuge in the domestic washing machine. The water absorption percentage is calculated from the dry weight of the sample and the wet weight after centrifugation according the equation given below:

Water absorption % = (the wet weight − the dry weight)/the dry weight = 100

(iii) Serum concentration of isosorbide dinitrate

Serum is separated from 3 ml of blood sample, extracted with 4 ml n-hexane, concentrated, combined with ethyl acetate to adjust the volume 100 $\mu l$ and isosorbide dinitrate was determined by means of GC-ECD technique.

(iv) Serum concentration of BN

Serum is separated from 1 ml blood sample and BN is determined by the GC-MS technique according to the description in Journal of Chromatography, 338, 89-98 (1985).

(v) Serum concentration of progesterone

Serum is separated from 1 ml blood sample and progesterone was determined by the radioimmunoassay technique.

(vi) moisture transpiration

A cavity (for example, a round well of 4 cm diameter and 0.6 cm depth) is formed at the center of a thick glass plate and 3 ml water is poured into the well. A plaster (5 cm×5 cm) having a sufficient margin to paste up is stuck to the thick glass plate so that the well comes to the center of the plaster. They are allowed to stand under air-flowing conditions at 37° C. for 1 day and the moisture transpiration is calculated by dividing the weight reduction per day with the area of the plaster over the well (12.56 cm$^2$ in the above-stated well).

REFERENCE EXAMPLES

The hollow fiber sample (knitted fabric) and the adhesive solution were prepared by the following procedures:

(1) Hollow fiber sample (knitted fabric)

Dimethyl terephthalate (297 parts), ethylene glycol (265 parts), sodium 3,5-di(carbomethoxy)benzenesulfonate (11.7 mole % based on dimethyl terephthalate), manganese acetate tetrahydrate (0.084 part) and sodium acetate trihydrate (1.22 part) were charged into a glass flask equipped with a rectification column and ester interchange was effected according to the usual method. After distillation of the theoretical amount of methanol, the reaction mixture was transferred into a polycondensation flask equipped with a rectification column, combined with 0.090 part of 56% orthophosphoric acid solution in water as a stabilizer and 0.135 part of antimony trioxide as a polymerization catalyst, and they were allowed to react at 275° C. under normal pressure for 20 minutes, under reduced pressure of 30 mmHg for 15 minutes, then under high vacuum for 100 minutes. The final inner pressure was 0.39 mmHg and the resultant copolymer had 0.402 intrinsic viscosity, 200° C. softening point. After completion of the reaction the copolymer was made into chips according to a usual process.

The copolymer chips (15 parts) and polyethylene terephthalate chips of 0.640 intrinsic viscosity were mixed in a Nauter mixer (produced by Hosokawa Iron Works) for 5 minutes, dried at 110° C. in a nitrogen stream for 2 hours, then at 150° C. for 7 hours, and melt-kneaded and extruded through a twin screw extruder at 285° C. into chips. The chips had 0.535 intrinsic viscosity and 261° C. softening point.

The chips were dried in a usual manner, melt-spun through a spinneret having arc-shaped openings formed by clotting 2 places of each circular slit of 0.05 mm width and 0.6 mm diameter in a usual manner to form hollow fibers of 2:1 ratio of the outer diameter to the inner diameter (25% hollowness). This yarn is composed of 300 deniers/24 filaments and drawn at a ratio of 4.2 in a usual manner to give a multifilament yarn of 71 deniers/24 filaments. The multifilament yarn was knitted and the fabric was scoured, dried, treated with 1% caustic soda aqueous solution at the boiling point for 2 hours to give a knitted fabric of 15% alkali weight reduction, 3 seconds water absorption and 80% water absorption. The knitted fabric was thermoset at 100° C. for one minute after stretching 1.5 time longitudinally to form a knitted fabric of 38 g/m$^2$ unit area weight.

The resultant hollow fibers of the knitted fabric were observed to have fine pores which distribute all over the cross section with orientation along the fiber-extending direction and at least a part of which pass through to the hollow part.

(2) The adhesive solution

2-Ethylhexyl acrylate (97.4 parts), methacrylic acid (2.5 parts), polyethylene glycol (polymerization degree: 14) dimethacrylate (0.1 part), benzoyl peroxide (1.0 part) and ethyl acetate (100 parts) were charged in a reaction vessel equipped with a reflux condenser and a mechanical stirrer and polymerization was continued for 9 hours with slow stirring at 60° to 70° C. in a nitrogen atmosphere. The polymer conversion was 99.5 to 99.9%.

The resultant polymer solution was combined with ethyl acetate (500 parts) to adjust the solid content to about 20%.

EXAMPLE 1

The adhesive solution of the reference example 2 (500 parts) was mixed with progesterone (8.8 parts). The solution was cast on a release liner coated with silicones so that the adhesive layer (a) becomes 15 μm thick, and dried at 70° C. for 3 minutes, then at 110° C. for 3 minutes to give an adhesive layer containing progesterone. The amount of ethyl acetate remaining in the adhesive layer (a) was 18 ppm and the content of progesterone was 1.3 g/m².

A polyethylene terephthalate (PET) film (the film layer) of 1.3 μ thickness, 22 and 25 g/mm strength and 75 and 38% elongation in the two directions intersecting at right angle was contact-bonded to one surface of the adhesive layer (a). An adhesive layer (b) was prepared by casting the adhesive solution of the reference example (2) on a release liner so that the layer becomes 10 μm thick and drying it at 70° C. for 3 minutes, then at 110° C. for 3 minutes, then laminated to the free surface of the PET film. Further, the knitted fabric of hollow fibers of reference example (1)-3 was contact-bonded to the free surface of the adhesive layer (b). The adhesion force between the film layer and the knitted fabric was 164 g/12 mm in the laminate.

The plaster sheet was cut into pieces of 3 cm×3 cm and applied to shaved backs of rats weighing about 180 g. Blood was sampled at prescribed times given in Table 1 to determine serum progesterone by the radioimmunoassay (RIA) technique. The results of the assay and states of rat skins 24 hours after plaster application are shown in Table 1.

EXAMPLES 2 AND 3 AND COMPARATIVE EXAMPLES 1 AND 2

Example 1 was repeated except that films different in thickness were used instead of 1.3 μm PET film to prepare progesterone plasters and application test of them to rats was repeated. The results are given in Table 1.

TABLE 1

| | | Film layer | | | | | Serum concentration of progesterone (average values: n = 3) (unit: ng/ml) | | | | |
|---|---|---|---|---|---|---|---|---|---|---|---|
| | Thickness | Strength (g/mm) | | Elongation (%) | | Elongation | Application hours | | | | Skin 24 after |
| Preparations | (μm) | A | B | A | B | ratio | 0 | 2 | 8 | 24 | Application |
| Example 1 | 1.3 | 25 | 22 | 38 | 75 | 2.0 | 0.5 | 8.0 | 8.4 | 5.7 | No change at all |
| Example 2 | 1.8 | 30 | 36 | 37 | 77 | 2.1 | 0.5 | 7.6 | 7.7 | 7.0 | No change at all |
| Example 3 | 3.5 | 85 | 72 | 42 | 91 | 2.2 | 0.5 | 8.6 | 8.9 | 7.2 | Practically no change |
| Comparative example 1 | 6.0 | 73 | 104 | 45 | 96 | 2.1 | 0.5 | 9.0 | 8.0 | 7.1 | Erythema is seen |
| Comparative example 2 | 1.3 | 33 | 29 | 23 | 25 | 1.1 | 0.5 | 6.0 | 5.5 | 4.2 | No change at all but film breakage frequently occurred when the knitted fabric was press-bonded |

Note: A and B represent data in two directions intersecting at right angle.

TEST EXAMPLE 1

The adhesive solution of the reference example (2) was cast on a silicone-coated release liner to prepare the adhesive layers (a) different in thickness. All of the cast films were dried at 70° C. for 3 minutes, then at 110° C. for 3 minutes and the amount of ethyl acetate remaining in the adhesive layer (a) was determined by gas chromatography (GC).

PET films (the film layer) having the thickness, strength and elongation described in Table 2 were press-bonded to one surface of the adhesive layer (a), respectively and another adhesive layers (b) shown in Table 2 were press-bonded to the other free surface of the film layer. Further, the hollow fiber sample (knitted fabric) of Reference example (1) was bonded to the other free surface of the adhesive layer as a backing sheet.

The sheets of the placebo plasters free from the drug were cut into pieces measuring 3 cm×3 cm and 12 pieces of the placebo plasters in which each piece is different from one another were applied to the backs of 5 healthy male adults (age: from 22 years to 45 years; body weight: from 55 kg to 82 kg) to observe the application feeling and skin rashes. As for the rashes, no reaction was judged to be 0; very slight erythema, 1; well defined erythema, 2 and the papule, 3; and the judge points of 5 members were summed up.

The test conditions and results of this test are summarized in Table 2.

Table 2 discloses that skin rashes become steeply large, when the film thickness exceeds about 5 μm (Nos. 4, 8), they suddenly decrease, when the film thickness becomes less than about 5 μm (for example, No. 1 through 3). As for application feeling, the films tend to be torn, when the film elongation falls down less than about 30% (No. 5) and the strength reduces less than about 8 g/mm (No. 6).

TABLE 2

Human application tests

| | Application conditions | | | | | | | | | Results | | |
|---|---|---|---|---|---|---|---|---|---|---|---|---|
| | Adhesive layer | | Film layer | | | | | Backing sheets | | | | |
| No. | Thickness (μm) | Remaining solvent (ppm) | Thickness (μm) | Strength (g/mm) A | B | Elongation (%) A | B | Elongation ratio | Thickness of adhesive layer (μm) | Adhesion force (g/12 mm) | Skin rash Total point of 5 persons | Application feeling |
| 1 | 10 | <10 | 1.3 | 25 | 22 | 38 | 75 | 2.0 | 10 | 167 | 1 | |
| 2 | " | " | 1.8 | 30 | 36 | 37 | 77 | 2.1 | " | 199 | 0 | |
| 3 | " | " | 3.5 | 85 | 72 | 42 | 91 | 2.2 | " | 178 | 6 | |
| 4* | " | " | 6 | 73 | 104 | 45 | 96 | 2.1 | " | 173 | 10 | peels from the skin |

TABLE 2-continued

Human application tests

| | Adhesive layer | | Film layer | | | | | Backing sheets | | Results | |
|---|---|---|---|---|---|---|---|---|---|---|---|
| | Thickness | Remaining solvent | Thickness | Strength (g/mm) | | Elongation (%) | | Elongation | Thickness of adhesive layer | Adhesion force (g/ | Skin rash Total point | |
| No. | (μm) | (ppm) | (μm) | A | B | A | B | ratio | (μm) | 12 mm) | of 5 persons | Application feeling |
| 5* | " | " | 1.3 | 31 | 29 | 18 | 25 | 1.4 | " | 184 | 0 | film frequently broke on productn. |
| 6* | " | " | 1.3 | 12 | 7 | 161 | 184 | 1.1 | " | 166 | 0 | film frequently broke on productn. |
| 7* | 1 | " | 1.3 | 25 | 22 | 38 | 75 | 2.0 | 10 | 167 | 0 | the plaster frequently peeled from the skin |
| 8* | 100 | 361 | 6 | 73 | 104 | 45 | 76 | 1.7 | " | 173 | 23 | |
| 9* | 70 | 147 | 3.5 | 85 | 72 | 42 | 91 | 2.2 | " | 178 | 12 | |

Note: A and B represent data in two directions intersecting at right angle.
*means a comparative example.

EXAMPLE 4

Example 1 was repeated except that the backing sheet was not employed and the adhesive layer containing progesterone was press-bonded to a PET film of 1.3 μm thickness and the plaster sheet was cut into pieces of 3 cm × 3 cm to prepare the plaster specimens for animal tests.

This plaster required a little time for application to the backs of test animals because it is too flexible, but caused no skin rash as in the plaster of Example 1.

EXAMPLE 5

Example 1 was repeated except that buprenorphine hydrochloride was used instead of progesterone and the adhesive layer containing buprenorphine hydrochloride was made 7 μm thick after drying to prepare a plaster sheet containing 0.56 g/m² buprenorphine hydrochloride. The sheet was cut into test pieces measuring 3 cm × 3 cm, the pieces were applied to shaved backs of 3 rats (n=3) and blood was sampled before plaster application, 2, 8 and 24 hours after application to determine the serum buprenorphine. The values were 0, 3.1, 5.7 and 5.6 (ng/ml) and good analgesic effect was observed with no skin rash at the application sites after removal of the plasters.

Additionally, although an adhesive layer as thin as 7 μm which cannot be found in conventional ones, the adhesion force was found to be sufficient and the amount of expensive buprenorphine hydrochloride could be largely reduced.

EXAMPLE 6

Another plaster was prepared in the same manner as in Example 5 except that nicotine was used in place of buprenorphine hydrochloride. The plaster was applied to rat backs and no rash was confirmed.

EXAMPLE 7

Example 5 was repeated except that estradiol was used instead of buprenorphine hydrochloride to prepare another plaster. The plaster was applied to rat backs to confirm no rash.

TEST EXAMPLE 2

No. 3 of Test example 1 was repeated the adhesive layer (b) of 10 μm thickness comprising a PET film of 3.5 μm thickness and the backing sheet was replaced with the adhesive layer (b) bearing stripes of adhesive which will be illustrated below to make human application tests. At this time, the adhesion force between the film layer and the backing sheet was 47 g/12 mm with no peeling during the application, while skin rash was good, 3 points (sum up of 5 persons).

Preparation of the adhesive layer (b) bearing stripes of adhesive lines: The adhesive solution of the reference example (2) was continuously extruded into strings in an equal interval on a release liner which moves continuously so that the adhesive forms stripes or bands.

The resultant adhesive layer had 10 μm average thickness and stripes of 2 mm wide adhesive lines with 3 mm intervals.

EXAMPLE 8

A backing sheet was prepared by impregnating a woven polyester fabric of 32 g/m² unit area weight with 10% PVA (polymerization degree: 500) solution in water so that the PVA content becomes 25 wt. % based on the fabric after drying. The stiffness of the fabric impregnated with PVA was 6.2 cm³/100.

The woven fabric which was impregnated with PVA and dried was wetted with water and press-bonded to a PET film having the same thickness, strength and elongation as in Example 1 (the film layer) and dried at 60° C. to give a laminate.

The laminate had 5 g/12 mm adhesion force beween the ilm and the fabric and 4.8 cm³/100 stiffness. Then, the adhesive layer (a) which was prepared in Example 1, of 15 μm thickness, containing 1.3 g/m² of progesterone, was press-bonded to the free surface of the film layer of the laminate.

The plaster sheet was cut into pieces of 3 cm × 3 cm, the pieces were applied to shaved backs of rats weighing about 180 g, then the woven fabric of the backing sheet was peeled off. No PVA remained on the film surface.

Blood was sampled at the prescribed times shown in Table 1 and serum progesterone was determined by the RIA technique and the rat skins were observed 24 hours after application. The results are given in Table 3.

EXAMPLES 9 AND 10 AND COMPARATIVE EXAMPLES 3 AND 4

Example 8 was repeated except that the PET film of 1.3 μm thickness was replaced with films of different thickness to prepare progesterone plasters. The application was tested with rats and the results are given in Table 3.

TABLE 3

Serum concentration of progesterone (average values: n = 3)
(unit: ng/ml)

| Preparations | Film layer | | | | | | Application hours | | | | Skin 24 after Application |
|---|---|---|---|---|---|---|---|---|---|---|---|
| | Thickness (μm) | Strength (g/mm) | | Elongation (%) | | Elongation ratio | 0 | 2 | 8 | 24 | |
| | | A | B | A | B | | | | | | |
| Example 8 | 1.3 | 25 | 22 | 38 | 75 | 2.0 | 0.5 | 7.6 | 7.9 | 6.5 | |
| Example 9 | 1.8 | 30 | 36 | 37 | 77 | 2.1 | 0.5 | 7.3 | 6.8 | 6.1 | No change at all |
| Example 10 | 3.5 | 85 | 72 | 42 | 91 | 2.2 | 0.5 | 9.3 | 10.4 | 7.3 | Practically no change |
| Comparative example 3 | 6.0 | 73 | 104 | 45 | 96 | 2.1 | 0.5 | 8.8 | 7.7 | 7.6 | Erythema was seen |
| Comparative example 4 | 1.3 | 31 | 29 | 18 | 25 | 1.4 | 0.5 | 4.2 | 3.9 | 2.3 | No change at all but removal of plasters was difficult due to film breakage |

Note: A and B represent data in two directions intersecting at right angle.

TEST EXAMPLE 3

An adhesive layer (a) free from drug was prepared in the same manner as in Test example 1 and the amount of ethyl acetate remaining in the adhesive layer (a) was determined by GC.

A polyester woven fabric of 32 g/m² unit area weight was impregnated with 10% PVA (polymerization degree: 500) solution in water in the amounts described in Table 4 to prepare the backing sheet containing different amounts of PVA based on the fabric after drying.

The dried backing sheet and the PET films of different thickness were press-bonded as in Example 8 to prepare laminates. The adhesion forces between the films and the fabric were measured.

The laminates and the adhesive layers prepared previously were combined as given in Table 4 and the adhesive layer was press-bonded to the free surface of the film in the laminates.

The placebo plaster sheet was cut into pieces of 3 cm × 3 cm and 12 pieces of placebo plasters in which each plaster is different from one another were applied to the backs of 5 healthy adult males (age: from 22 years to 45 years; body weight: from 55 to 82 kg) to observe the application feeling and skin rashes 24 hours after application. As for the rashes, no reaction was judged to be 0; very slight erythema, 1; well defined erythema, 2 and the papule, 3; then the judge points of 5 members were summed up.

The test conditions and results of this test are summarized in Table 4.

Table 4 evidently shows that skin rashes suddenly expands large with over about 5 μm film thickness (No. 4, 8), while less than about 5 μm thickness steeply lowers the rashes (for example, No. 1 through 3). As for the application feeling, less than about 30% film elongation (No. 5) or less than about 8 g/mm strength (No. 6) cause fragile film breakage during the plaster handling. Further, high thickness of the adhesive layers expands skin rashes (No. 8, 9).

EXAMPLE 11

Example 8 was repeated except that progesterone was replaced with buprenorphine hydrochloride and the adhesive layer (a) containing buprenorphine hydrochloride was set 7 μm thick after drying to prepare a plaster containing 0.56 g/m² buprenorphine hydrochloride. The plaster was cut into pieces measuring 3 cm × 3 cm and they were applied to shaved backs of rats (n=3). Blood was sampled before application, 2, 8 and 24 hours after application to determine serum buprenorphine and the results were 0, 4.2, 6.1 and 5.7 (ng/ml) and showed good analgesic effect. There was found no skin rash on the plaster application sites after the plaster pieces were removed.

Moreover, regardless of using an extremely thin adhesive layer of 7 μm thickness which was not seen in existing plasters, the plaster had sufficient adhesion force to the skin and the amount of expensive buprenorphine hydrochloride could be largely reduced.

TABLE 4

Human application tests
Application conditions

| No. | Adhesive layer | | Film layer | | | | | | Backing sheets | | Results | |
|---|---|---|---|---|---|---|---|---|---|---|---|---|
| | Thickness (μm) | Remaining solvent (ppm) | Thickness (μm) | Strength (g/mm) | | Elongation (%) | | Elongation ratio | Amount of PVA (wt %) | Adhesion force (g/ 12 mm) | Skin rash Total point of 5 persons | Application feeling |
| | | | | A | B | A | B | | | | | |
| 1 | 10 | <10 | 1.3 | 25 | 22 | 38 | 75 | 2.0 | 25 | 5 | 0 | |
| 2 | " | " | 1.8 | 30 | 36 | 37 | 77 | 2.1 | " | 5 | 0 | |
| 3 | " | " | 3.5 | 85 | 72 | 42 | 91 | 2.2 | " | 5 | 4 | |
| 4* | " | " | 6 | 73 | 104 | 45 | 96 | 2.1 | " | 4 | 9 | peels from the skin |
| 5* | " | " | 1.3 | 31 | 29 | 18 | 25 | 1.4 | " | 5 | 0 | film frequently broke |
| 6* | " | " | 1.3 | 12 | 7 | 161 | 184 | 1.1 | " | 5 | 0 | on the application |
| 7* | 1 | " | 1.3 | 25 | 22 | 38 | 75 | 2.0 | 25 | 5 | 0 | Frequently peeled from the skin |
| 8* | 100 | 361 | 6 | 73 | 104 | 45 | 76 | 1.7 | " | 4 | 21 | |
| 9* | 70 | 147 | 3.5 | 85 | 72 | 42 | 91 | 2.2 | " | 5 | 11 | |

Note: A and B represent data in two directions intersecting at right angle.
*means a comparative example.

EXAMPLE 12

Example 11 was repeated except that the buprenorphine hydrochloride was replaced with nicotine to prepare a plaster. The plaster was applied to rat backs to confirm no skin rash.

EXAMPLE 13

Example 11 was repeated except that the buprenorphine hydrochloride was replaced with estradiol to prepare a plaster. The plaster was applied to rat backs to confirm no skin rash.

EXAMPLE 14

Example 8 was repeated except that the PET film was replaced with a PET film which had 1.3 μm thickness, 22 and 32 g/cm and 75 to 35% strengths and elongations in the two rectangular cross directions, respectively, and contains, in the film as solid fine particles, 0.08% by weight, based on the film total weight, of synthetic silica of 0.70 μm average particle size, to prepare a laminate.

The adhesive force between the film and the woven fabric was 5 g/12 mm. The stiffness was 4.8 cm$^3$/100. The adhesive layer (a) of 15 μm thickness, containing 1.3 g/m$^2$ of progesterone was press-bonded to the free surface of the film layer of the laminate.

The plaster sheet was cut into pieces of 3 cm × 3 cm and the pieces were applied to shaved backs of rats weighing about 180 g, then the woven fabric as a backing sheet was peeled off. There was substantially no PVA remaining on the surface of the film. Then, blood was sampled at the times prescribed in Table 5 and serum progesterone was determined by the RIA technique and the rat skins were observed 24 hours after applications. The results are given in Table 5.

EXAMPLES 15 THROUGH 17 AND COMPARATIVE EXAMPLES 6 AND 7

The films described in Table 5 were used to prepare progesterone plasters in the quite same manner as in Example 14. The plasters were applied to rat backs and the results are shown in Table 5.

plaster containing 0.56 g/m$^2$ buprenorphine hydrochloride. The plaster was cut into pieces measuring 3 cm × 3 cm and they were applied to shaved backs of rats (n=3). Blood was sampled before application, 2, 8 and 24 hours after application to determine serum buprenorphine and the results were 0, 4.3, 6.0 and 5.8 (ng/ml) with good analgesic effect. There was found no skin rash on the plaster application sites after the plaster pieces were removed.

Moreover, regardless of using an extremely thin adhesive layer of 7 μm thickness which was not seen in existing plasters, the plaster had sufficient adhesion force to the skin and the amount of expensive buprenorphine hydrochloride could be largely reduced.

TEST EXAMPLE 4

Placebo preparations in Example 11 and Example 18 were cut into pieces measuring 7.1 cm$^2$ and applied to human right chests of 5 persons each placebo preparation for 48 hours. Skin stimulation was observed 1 hour after removal of the preparations to evaluate the skin stimulation. As for the rashes, no reaction was judged to be 0; very slight erythema, 0.5; well defined erythema, 1.0; erythema and edema 2 and erythema, edema and papule, 3 and the groups were compared with the sum-ups of individual values in each group. As a result, the placebo in Example 11 was 2.0 point, while that in Example 18 was 1.0 and Example 18 was judged to be less stimulant.

EXAMPLE 19

Example 18 was repeated except that the buprenorphine hydrochloride was replaced with nicotine to prepare a plaster. The plaster was applied to rat backs to confirm no skin rash.

EXAMPLE 20

Example 18 was repeated except that the buprenorphine hydrochloride was replaced with estradiol to prepare a plaster. The plaster was applied to rat backs to confirm no skin rash.

EXAMPLE 21 AND COMPARATIVE EXAMPLE

TABLE 5

| | | Film layer | | | | Solid fine particles | Progesterone concentration (m = 3, ng/ml) Application hours | | | | |
|---|---|---|---|---|---|---|---|---|---|---|---|
| Preparations | Thickness (μm) | Strength (g/mm) A | B | Elongation (%) A | B | Elongation ratio | (substance) Amount (wt %)/ average size (μm) | 0 | 2 | 8 | 24 | Skin 24 hours after application |
| Example 14 | 1.3 | 22 | 32 | 75 | 35 | 2.1 | synthetic silica 0.08/0.70 | 0.5 | 7.6 | 7.9 | 6.5 | No change substantially |
| Example 15 | 1.8 | 36 | 48 | 77 | 75 | 1.9 | synthetic silica 0.1/0.45 | 0.5 | 7.3 | 6.8 | 6.1 | No change substantially |
| Example 16 | 3.5 | 72 | 59 | 91 | 120 | 1.3 | talc | 0.5 | 9.3 | 10.4 | 7.3 | Practically no change |
| Example 17 | 1.8 | 25 | 33 | 40 | 30 | 1.3 | synthetic silica 2.0/0.45 | 0.2 | 2.1 | 2.4 | 2.0 | Serum concentration was relatively low |
| Comparative example 6 | 6.0 | 104 | 120 | 96 | 70 | 1.4 | talc 0.1/0.75 | 0.5 | 8.8 | 7.7 | 7.6 | Erythema was seen |
| Comparative example 7 | 1.3 | 29 | 55 | 26 | 5 | 5.2 | synthetic silica 0.08/0.70 | 0.5 | 4.2 | 3.9 | 2.3 | No change at all but removal of plaster was difficult due to film breakage |

Note: A and B indicate 2 substantially rectangular directions.

EXAMPLE 18

Example 14 was repeated except that progesterone was replaced with buprenorphine hydrochloride and the adhesive layer (a) containing buprenorphine hydrochloride was set 7 μm thick after drying to prepare a

8

The plaster was composed of the first 1.8 μm thick PET film as the backing sheet, the second 1.3 μm thick PET film which is the same one as used in Example 14 as the film layer, and the adhesive layer (a) of 10 μm thickness, containing 1.3 g/m² progesterone and the backing sheet was press-bonded to the film layer all over the surface through the adhesive layer (b) of 10 μm thickness, which was prepared from the adhesive solution in reference example (2).

The PET films used in the laminate included 0.08% by weight of synthetic silica of 0.7 μm average particle size as the solid fine particles. The plaster sheet (Example 20) was measured on its moisture evaporation and found to be 12.7 mg/day. cm².

Further, a polyester film of 12 μm thickness was laminated with the adhesive layer of 10 μm thickness same as in Example 21, containing progesterone were laminated for comparison (comparative example 8).

The resultant plaster showed only 7.3 mg/day. cm² moisture evaporation.

EXAMPLE 22

As the backing sheet, a knitted fabric of finely pored polyester hollow fibers used as the backing sheet in Example 1 was inserted between the film used as the backing sheet in Example 20 (the film layer (b)) and the film layer (a) and these 3 layers were laminated with acrylic adhesive layers (b1 and b2) of 10 μm thickness. Then, the adhesive layer (a) containing the drug, which was used in Example 20, was press-bonded on the film layer (a) of the laminate.

The plaster sheet showed a moisture evaporation of 19.4 mg/day. cm².

COMPARATIVE EXAMPLE 9

Example 5 was repeated except that a polyethylene film of 7 μm thickness, 20 g/mm strength and 276% elongation in one direction was used instead of a PET film of 1.3 μm thickness to produce a plaster containing 0.56 g/m² of buprenorphine hydrochloride. The plaster was cut into pieces measuring 3 cm × 3 cm, applied as in Example 5 and found to show serum concentrations, 0, 0.5, 1.2 and 3.8 ng/ml before application, 2, 8 and 24 hours after application, respectively. There was no skin rash on the application site of the skin after removal of the plaster.

The moisture permeability of the plaster was 133 g/day. cm².

TEST EXAMPLE 5

The plaster sheets prepared in Examples 21, 22 and Comparative example 8 and 9 were cut into pieces of 7.1 cm² and the pieces of each plaster were applied to right chests of 2 humans for 48 hours and the states were observed 1 hour after removal of the plaster. The results are shown in Table 6.

TABLE 6

| | Observation 1 hour after removal |
|---|---|
| Example 20 | Substantially no change in both |
| Example 21 | Substantially no change in both |
| Comparative example 8 | Erythema was noticed in both |
| Comparative example 9 | Substantially no change in both |

The plasters according to the present invention was proved to be excellent because the skins caused substantially no change before and after application.

EXAMPLE 23

The adhesive layer (b2) which was obtained by coating the adhesive solution shown in Reference example in 15 μm thickness was laminated onto the 1.3 μm thick PET film (b) used in Example 14, then a backing sheet of hollow fiber-knitted fabric (38 g/m² unit area weight) and the adhesive (b1) which was prepared by coating the adhesive solution shown in the Reference example in 40 μm thickness were contact-bonded thereto, and finally the 1.3 μm thick PET film used in Example 14 was contact-bonded to the free surface of the adhesive layer (b1).

Meanwhile, an adhesive layer of 10 μm thickness containing 1.13 g/m² buprenorphine hydrochloride, which was obtained as in Example 1, was laminated onto the surface of the PET film (a) in the above-stated laminate, thus a plaster containing 2.8 mg buprenorphine hydrochloride per 5 cm × 5 cm area was obtained. The plaster was cut into pieces of 4.5 cm² and applied to the shaved necks of rats weighing 150 grams on the average (n=5) to determine the serum concentration of buprenorphine hydrochloride by sampling blood before application, 2, 8 and 24 hours after application. The results were 0, 1.9, 2.7 and 3.4 ng/ml, respectively and showed good analgesic effect.

This plaster had good handleability and no change was observed in the skin after removal of the plaster, proving reduced skin stimulation.

POSSIBILITY OF INDUSTRIAL UTILITY

The plasters according to the present invention can be utilized in the clinical field of the medical treatment as a plaster for transdermal absorption of a clinically effective amount of drugs with skin rashes reduced and high peeling resistance.

Particularly, the plasters of the present invention, combined with the backing sheet and the sheet-like body are improved in their handleability and can be easily and simply applied even by aged patients.

We claim:

1. A plaster comprising:
    (1) a film layer which comprises a polyester film of 0.5 to 4.9 μm thickness, 8 to 85 g/mm strength, respectively in the two directions intersecting substantially at right angles, 30 to 150% elongation, in the two directions intersecting substantially at right angles and an elongation ratio of A to B of 1.0 to 5.0, wherein A and B represent data in two directions intersecting at right angles, and A is greater than B, and wherein said polyester film comprises 0.01 to 1.0% by weight, based on the total weight of said polyester film, of solid fine particles in which
        (a) the average particle size is 0.001 to 3.0 μm, and
        (b) the average particle size is substantially not more than 1.5 times the thickness of said polyester film; and
    (2) an adhesive layer (a) which is composed of an adhesive containing transdermally absorbable drugs and further wherein said adhesive layer (a) is laminated on said film layer over the surface in a 2 to 60 μm thickness.

2. The plaster according to claim 1 wherein said adhesive layer (a) is an acrylic resin adhesive.

3. The plaster according to claim 1 wherein said elongation ratio is 1.0 to 3.0.

4. The plaster according to claim 1 wherein said transdermally absorbable drug comprises one or more compounds selected from the group consisting of isosorbide dinitrates, nitroglycerin, buprenorphine, estradiol, progesterone, ketotifen, vinpocetine, nicotine and morphine 5. A plaster comprising:
(1) a film layer which comprises a polyester film having a 0.5 to 4.9 μm thickness, 8 to 85 g/mm strength, respectively in the two directions intersecting substantially at right angles, 30 to 150% elongation in the two directions intersecting substantially at right angles and an elongation ratio of A to B of 1.0 to 5.0, wherein A and B represent data in two directions intersecting at right angles, and A is greater than B, and wherein said polyester film comprises 0.01 to 1.0% by weight, based on the total weight of said polyester film, of solid fine particles in which
   (a) the average particle size is 0.001 to 3.0 μm and
   (b) the average particle size is not more than 1.5 times the thickness of said polyester film; and
(2) an adhesive layer (a) comprising a transdermally absorbable drug and wherein said adhesive layer (a) is laminated on a front surface of said film layer in 2 to 60 μm thickness, and
(3) a backing sheet which is adhered, with an adhesive force of over 3 g/12 mm, through an adhesive layer (b), wherein said adhesive layer (b) is partially or entirely laminated to a back side of said film layer, and wherein said adhesive layer (b) is 2 to 100 μm thick.

6. The plaster according to claim 5 wherein said adhesive layer (a) is an acrylic resin adhesive.

7. The plaster according to claim 5 wherein said adhesion force is 3 g/12 mm to 20 g/12 mm.

8. The plaster according to claim 5 wherein said adhesion force is greater than 20 g/12 mm.

9. The plaster according to claim 7 or claim 8 wherein said adhesion force is less than that between said film layer and said adhesive layer (a).

10. The plaster according to claim 5 wherein said backing sheet is a film, nonwoven fabric, paper-like substance; a cloth made of material selected from woven and knitted fabrics; or a combination thereof.

11. The plaster according to claim 5 wherein said backing sheet is a microporous film or a woven or knitted fabric of 10 to 300 g/cm² units area weight.

12. The plaster according to claim 1 or claim 11 wherein said knitted fabric is made from hollow filaments which have through-holes radially extending toware the outer periphery and wherein said filaments are 4 to 45 μm thick.

13. The plaster according to claim 5 wherein said adhesive layer (b) is composed of an adhesive, wherein a major component of the adhesive is selected from the group consisting of polyvinyl alcohol, a vinyl acetate polymer, and both polyvinyl alcohol and a vinyl acetate polymer.

14. The plaster according to claim 5 wherein said adhesive layer (b) is composed of an acrylic resin adhesive.

15. The plaster according to claim 13 or claim 14 wherein said adhesive layer (b) is 2 to 100 μm thick.

16. The plaster according to claim 5 wherein said elongation ratio is 1.0 to 3.0.

17. The plaster according to claim 5 wherein its moisture evaporation rate is over 10 mg/day/cm².

18. The plaster according to claim 1 wherein said drug is one or more compound(s) selected from the group consisting of isosorbide dinitrates, nitroglycerin, buprenorphine, estradiol, progesterone, ketotifen, vinpocetine, nicotine and morphine.

19. A plaster comprising:
(1) a polyester film layer (a) which is composed of a film having a 0.5 to 4.9 μm thickness, 8 to 85 g/mm strength, respectively in the two directions intersecting substantially at right angles, 30 to 150% elongation in the two directions intersecting substantially at right angles and an elongation ratio of A to B of 1.0 to 5.0, wherein A and B represent data in two directions intersecting at right angles, and A is greater than B, and wherein said polyester film comprises 0.01 to 1.0% by weight, based on the total weight of said polyester film, of solid fine particles in which
   (a) the average particle size is 0.001 to 3 μm, and
   (b) the average particle size is substantially not more than 1.5 times the thickness of said polyester film; and
(2) an adhesive layer (a) which comprises a transdermally absorbable drug and said adhesive later (a) is laminated on a front surface of said film layer in 2 to 60 μm thickness,
(3) a backing sheet which is adhered, with an adhesive force (a1) of over 20 g/12 mm, through an adhesive layer (b1), wherein said adhesive layer (b1) is partially or entirely laminated to a back surface of the film layer(a), and
(4) a film layer (b) which comprises a film having 0.5 to 4.9 μm thickness, 8 to 85 g/mm strengths, respectively in the two directions intersecting substantially at right angles, 30 to 150% elongations, respectively in the two directions intersecting substantially at right angles and an elongation ratio of A to B of 1.0 to 5.0, wherein A and B represent data in two directions intersecting at right angles, and A is greater than B, and wherein said film layer (b) is partially or entirely laminated with an adhesion force (b1) of over 3 g/12 mm, through an adhesive layer (b2) to said backing sheet on a side surface not bonded to the adhesive layer (b1).

20. The plaster according to claim 19 wherein said adhesive layer (a) is an acrylic resin adhesive.

21. The plaster according to claim 19 wherein said adhesion force b1 is from 3 g/12 mm to 20 g/12 mm.

22. The plaster according to claim 19 wherein said adhesion force b1 is greater than 20 g/12 mm.

23. The plaster according to claim 19 or claim 20 wherein said adhesion force b1 is less than said adhesion force a1.

24. The plaster according to claim 19 wherein said backing sheet is a nonwoven fabric, paper-like substance, a cloth made of material selected from woven and knitted fabrics, or a combination thereof.

25. The plaster according to claim 19 wherein said backing sheet is a microporous film or a woven or knitted fabric of 10 to 300 g/cm² unit area weight.

26. The plaster according to claim 24 or claim 25 wherein said knitted fabric is made from hollow filaments which have through-holes radially extending toward the outer periphery and 4 to 45 μm filament thickness.

27. The plaster according to claim 19 wherein said adhesive layers (b1) and (b2) are composed of an adhesive containing polyvinyl alcohol a vinyl acetate polymer or both as a major component.

28. The plaster according to claim 19 wherein said adhesive layers (b1) and (b2) are composed of an acrylic resin adhesive.

29. The plaster according to claim 27 or claim 28 wherein said adhesive layers (b1) and (b2) are 2 to 100 μm thick.

30. The plaster according to claim 19 wherein said elongation ratio is 1.0 to 3.0.

31. The plaster according to claim 19 having a plane backing body which is adhered with an adhesion force ranging from 3 g/12 mm to 20 g/12 mm, through an adhesive layer (c) partially or entirely to said film layer (b) on the surface not bonded to said backing sheet.

32. The plaster according to claim 19 wherein said drug is one or more compound(s) selected from the group consisting of isosorbide dinitrates, nitroglycerin, buprenorphine, estradiol, progesterone, ketotifen, vinpocetine, nicotine and morphine.

33. The plaster according to claim 1 wherein said plaster has a moisture transpiration rate of greater than 10 to 80 mg/day/cm$^2$.

* * * * *